United States Patent [19]

Couillard

[11] Patent Number: 4,787,746
[45] Date of Patent: Nov. 29, 1988

[54] REFRACTOMETRIC DETECTOR FOR LIQUID PHASE CHROMATOGRAPH

[75] Inventor: Francois Couillard, Cpuk, France

[73] Assignee: Compagnie Europeenne D'Instrumentation Cedi, Societe Anonyme Francaise, Lannemezan, France

[21] Appl. No.: 41,732

[22] Filed: Apr. 22, 1987

[51] Int. Cl.$^4$ .............................................. G01B 9/02
[52] U.S. Cl. .................................................. 356/361
[58] Field of Search ............................... 356/361, 362

[56] References Cited

U.S. PATENT DOCUMENTS 3,680,963  8/1972  Edwards et al. .................... 356/361

OTHER PUBLICATIONS

Boensch, "Photoelectric Determination of Fringe Fraction in the Koesters Interferometer", *Feinwenk Technik & Messtechnik*, vol. 84, No. 7, pp. 350–353, 11/76.
Bergquist et al. "Static and Dynamic Transducer Calibrations Using Optical Interferometric Technique", *Conference on the Evaluation and Calibration of Ultrasonic Transducers*, London, England, May 1977, pp. 116–122, IPC Business Press.

Primary Examiner—Davis L. Willis
Assistant Examiner—Matthew W. Koren
Attorney, Agent, or Firm—Browdy and Neimark

[57] ABSTRACT

Chromatograph in high performance liquid phase comprising a monochromatic light source emitting a beam which, after splitting, is divided into two parallel beams which go respectively through two cuvettes, the one containing a reference liquid, the other the measurement liquid. The two beams on coming from the cuvettes go into a detection unit. After splitting, each of beams R, M is divided into a system P with a semireflecting surface SR, a part going into one of the cuvettes CR, CM and being reflected by the rear of the cuvette forming a mirror MC to come back to semireflecting surface SR along a reverse path, the other part of the beam coming to be reflected on a mirror MR, at right angles to each beam, moved by a piezoelectric device PZ. The two parts of each beam coming from cuvettes CR, CM and coming from mirror MR moved by a piezoelectric device are joined in semireflecting system P, SR to reach a photodiode DM, DR sending the emitted signals to a phasemeter measuring the phase shift and the number of cycles k of phase shift between beams. The signals emitted by photodiode SM of the measurement beam are sent to a generator G exciting the piezoelectric system PZ, source S being a laser source.

4 Claims, 1 Drawing Sheet

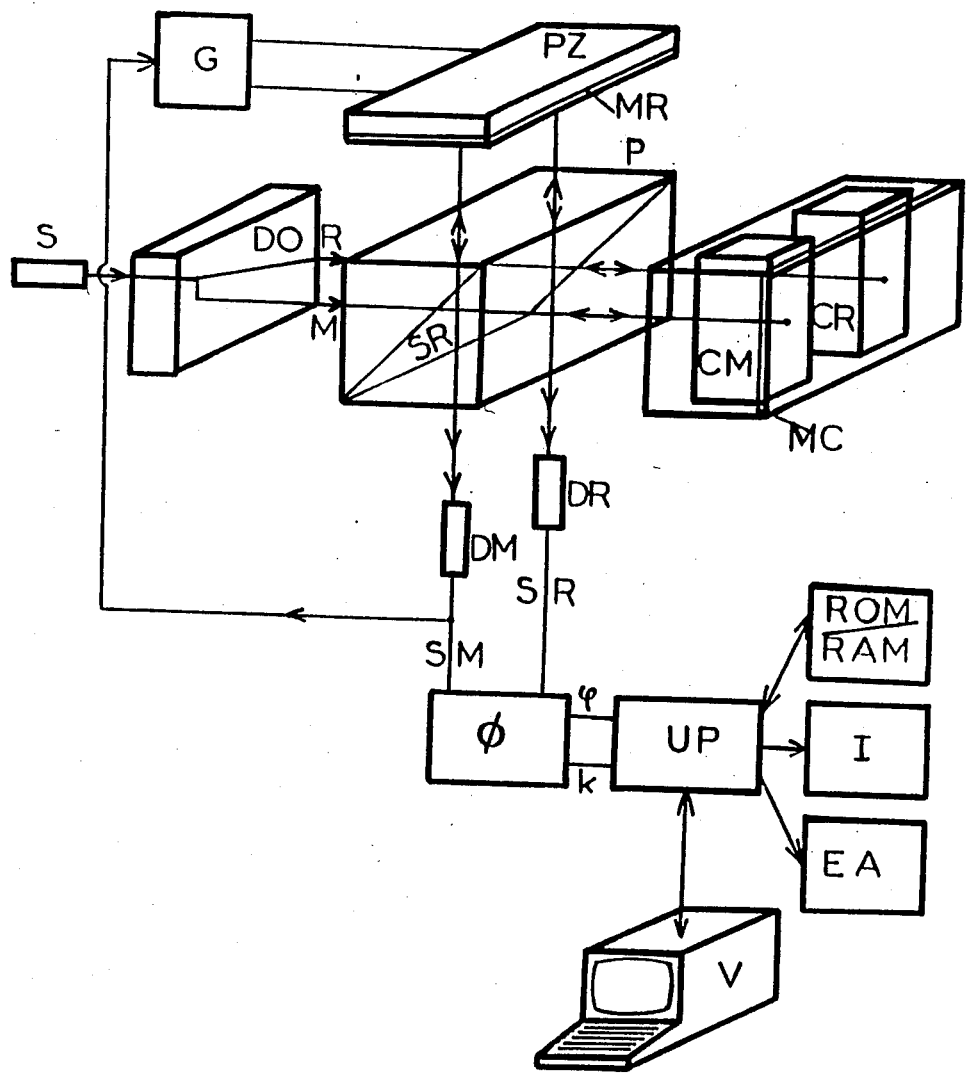

REFRACTOMETRIC DETECTOR FOR LIQUID PHASE CHROMATOGRAPH

FIELD OF INVENTION

This invention has as its object improvements in high performance liquid phase chromatographs (HPLC).

BACKGROUND OF THE INVENTION

At present most detectors used are photometers and refractometers, and more rarely, for very specific applications, electrochemical, conductimetric detectors or others.

Photometers offer the advantages of a high sensitivity and a great stability. They can be used in all cases where the eluates to be detected absorb light in the range of wavelengths between about 190 and 700 nm. But these photometers have major drawbacks: they are not universal, and in the same analysis, it is possible to encounter not only eluates that absorb light at different wavelengths or which practically do not absorb light, which particularly in preparative chromatography can have the drawback of allowing impurities to pass unperceived.

What is more, in this case of preparative chromatography, the photometer is quickly saturated at about an optical density on the order of 2.

By dividing the length of the optical path in the cuvette by 10, this drawback is reduced, but the device loses even more sensitivity.

In regard to refractometers, they have the essential advantage of being practically universal. Most of the devices now marketed are with light beam deviation by double prismatic cuvette or container with circulation. In these detectors, a light source projects a beam onto a double photodetector after having successively gone through a diaphragm, optional concentration lenses, a turning glass plate with parallel faces to adjust the optical zero of the device, i.e., to balance the light intensity illuminating the two photodetectors, a double prismatic cuvette, one for a reference liquid, the other for the phase to be analyzed.

When the index of refraction of this latter varies, the prismatic section of the two successive cuvettes is such that the beam deviates from one photodetector to the next, according to the sign of the difference of the indices between the two cuvettes. Now, in some cases, particularly in preparative chromatography, where it is possible to encounter high concentrations in one of the two cuvettes, or if an elution gradient is created, the variations of the indices can be such that the beam deviates up to the saturation of the instrument, i.e., the deviated beam illuminates only one of the two cells. Thus, the chromatogram is clipped and several peaks with a common base can be undistinguished. Just as for photometers, it is possible to reduce the drawbacks by reducing the deviations, but at the price, here, too, of loss of sensitivity. The saturation is then avoided, but small peaks, i.e., impurities, are no longer distinguished when using preparative chromatography.

Regardless of the efforts made, the problems created by a gradient are encountered.

A monochromatic source refractometer system has also been proposed whose beam is divided to go through two cuvettes in parallel, for a reference liquid and the phase to be analyzed, then the two beams are gathered to illuminate a photodetector. Interferences are produced because of the variation of the optical path on the measurement side as a function of the variation of the index. It can be considered that the sine wave followed by the intensity is linear in the vicinity of the zero index difference; this gives an acceptable sensitivity but does not solve the problems of saturation and use of gradient, and as in the previous cases, the saturation can be avoided to the detriment of sensitivity.

SUMMARY OF THE INVENTION

This invention therefore has as its object to avoid the drawbacks listed above and particularly by making sensitivity and saturation compatible, especially for preparative chromatography, and making it possible to use an elution gradient both in analytical and preparative chromatography.

To do this according to the invention, an interferential differential refractometer is used each of whose (reference or measurement) cuvettes will participate, independently of one another, in two independent interferometer systems, but fed light by the same source (laser, for example).

The photometric detection of the two interferometers will be achieved by two independent photodetectors. It is understood that in such a system each photodetector receives a light intensity which is a sine wave function of the difference of the indices of refraction between the reference and measurement cuvettes.

Consequently, if in one of the cuvettes the index of refraction gradually varies in very great proportions, for example as a gradient, the corresponding photodetector receives a light intensity with sine wave variation, which means that there is available phase data between the measurement and reference which will be a function, to within $2k\pi$, of the difference of the index of refraction between the two cuvettes.

If this difference becomes very great, nothing changes, and the instrument, at the detection stage, never reaches saturation. Therefore, it is possible to speak of infinite measurement dynamics, although the index of refraction is a finite magnitude.

For this to be significant, a determination will be made of the two products or mixtures of products of extreme indices which can be envisaged to define the memory capacity of the data processing system which is simply to store the phase shifts to within $2k\pi$, by determining k, for example, by the derivative of the detected signal.

The detector according to the invention is entirely computerized and the elution gradient can be used. Since saturation is no longer expected, the chromatogram is drawn simply and clearly on an open-ended base line. The latter, as in an integrator, will be set at zero for the computation.

The chromatograms stored in memory can be displayed on a videographic display, on an analog recorder, on a graphic printer, or any other system of graphic display.

An automatic operation enables the device itself to select the best sensitivity for each peak and to record it in regard to each of them so that the chromatogram will remain within the limits of the display.

An electronic magnifier can enlarge, to the maximum sensitivity of the instrument, the base line and contour of the chromatogram, particularly to detect possible impurities, in particular in preparative chromatography.

It will be noted that the axis or axes of unused cuvettes according to th invention can make possible other measurements or detections, for example in ultraviolet spectrophotometry or fluometry.

DESCRIPTION OF THE DRAWING

The single figure diagrammatically represents a chromatographic detector device according to the present invention.

DETAILED DESCRIPTION OF THE INVENTION

For a better understanding of the technical characteristics and advantages of this invention, an embodiment will now be described, it being understood that it is no way limiting in regard to its mode of use and the applications which can be made of it. Reference will be made to the single figure which diagrammatically represents a chromatographic detector device according to the invention.

A monochromatic light source S, preferably a laser, emits a beam which by passage in optical dividing device DO is divided at the output into two parallel beams M and R, which go through double prism P with semi-reflecting plane surface SR between prisms at 45° in relation to the beams. A part of these latter beams is therefore reflected upward to be reflected along the same optical path by a mirror MR carried by a piezoelectric ceramic PZ and at right angles to the two beams. These latter are therefore reflected and come back to the double prism and, at least for a part of the light, go through it, including semireflecting surface SR, each to reach a photodiode DM, DR.

A part of each of the direct beams M and R coming from divider DO which goes through semireflecting surface SR reaches and goes through the two cuvettes, the one CR containing the reference liquid, the other CM the phase to be measured. The rear part of these cuvettes exhibits a mirror MC at right angles to the beams which therefore reflects them along the same path to come back to double prism P where at least a part of the light of each beam is reflected by semireflecting surface SR along the same path as the beams reflected by mirror MR.

The superposition according to each of these optical paths of light having gone through a cuvette and the corresponding liquid phase, and of the light reflected by the mirror moved by piezoelectric ceramic PZ, under the conditions described above, causes interferences, as said above, translated by photodiodes DM and DR into electric signals SM and SR brought to phasemeter $\phi$. Measurement signals SM are also sent for automatic control of the linearity to sawtooth excitation generator G of the piezoelectric ceramic.

Phase indication signals $\phi$ and k of the number of interference periods $2k\pi$ are collected at the output of the phasemeter. These signals are processed by a central unit such as a central computer unit UP connected to a ROM/RAM unit, an analog recorder EA and a video terminal V, as well as any other suitable data processing device, such as a printer I.

For a better functioning of the interferometers, it is possible to use a polarized light, laser or not.

Although the above described device according to the invention has been applied here to liquid phase chromatography, it is clear that such a differential refractometer can be used for other purposes, while remaining within the scope of the invention, such as the measurement of indices of refraction, for example in a control in a production line of chemical products.

What is claimed is:

1. A refractometric detector for high performance liquid chromatography comprising:
 a monochromatic light source for emitting a base;
 an optical dividing means for splitting said beam into two parallel beams;
 an optical system having a first mirror and a second mirror disposed perpendicular to the path of said two parallel beams;
 a piezoelectric device which moves said first mirror perpendicularly to its plane;
 a first cuvette containing a reference liquid, and a second cuvette containing a measurement liquid;
 a system having a semi-reflecting surface at 45° for receiving said two beams and reflecting a first part of said beams toward said cuvettes and a second part of said beams to said first mirror, said second part of said two beams being reflected by said first mirror so as to pass through said cuvettes, said second mirror being disposed so as to reflect said first part of said two beams after it passes through said cuvettes toward said semi-reflecting surface along a reverse path, said first and second parts being reflected by said first and second mirrors toward said semi-reflecting surface where said reflected first and second parts are joined together;
 a photodiode detection unit for receiving the joined beams from said semi-reflecting surface and for emitting measurement signals which excite the piezoelectric device, said unit comprising a photodiode means for each beam, said photodiode means sending the emitted signals to a phasemeter which measures the phase shift and the number of cycles of phase shift between the beams.

2. The detector of claim 1, wherein the phase signals and the number of cycles from the phasemeter are processed in a central processing unit connected to terminal for recording, displaying and or printing.

3. The detector of claim 2 wherein said monochromatic light source is a laser source.

4. The detector of claim 1 wherein said monochromatic light source is a laser source.

* * * * *